(12) United States Patent
Katzarov et al.

(10) Patent No.: US 11,813,074 B2
(45) Date of Patent: Nov. 14, 2023

(54) HAIR CONDITION DETERMINING DEVICE AND METHOD FOR PROVIDING HAIR CONDITION INFORMATION

(71) Applicant: Henkel AG & Co. KGaA, Duesseldorf (DE)

(72) Inventors: Jordan Katzarov, Duesseldorf (DE); Adrian Lehanne, Berlin (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 354 days.

(21) Appl. No.: 16/771,468

(22) PCT Filed: Dec. 7, 2018

(86) PCT No.: PCT/EP2018/083912
§ 371 (c)(1),
(2) Date: Jun. 10, 2020

(87) PCT Pub. No.: WO2019/115370
PCT Pub. Date: Jun. 20, 2019

(65) Prior Publication Data
US 2021/0068744 A1    Mar. 11, 2021

(30) Foreign Application Priority Data
Dec. 11, 2017    (DE) .................. 10 2017 222 421.5

(51) Int. Cl.
*A61B 5/00*    (2006.01)
*A61B 5/103*    (2006.01)

(52) U.S. Cl.
CPC ............ *A61B 5/448* (2013.01); *A61B 5/0004* (2013.01); *A61B 5/0022* (2013.01);
(Continued)

(58) Field of Classification Search
CPC ..................... A45D 2044/007; A61B 5/448
(Continued)

(56) References Cited

U.S. PATENT DOCUMENTS 7,443,508 B1    10/2008    Vrhel et al.
9,989,416 B2    6/2018    Lauriston
(Continued)

FOREIGN PATENT DOCUMENTS

EP    1629775 A1    3/2006
JP    2000116622 A    4/2000
(Continued)

OTHER PUBLICATIONS

EPO, International Search Report issued in International Application No. PCT/EP2018/083912, dated Mar. 6, 2019.

*Primary Examiner* — Fabricio R Murillo Garcia
(74) *Attorney, Agent, or Firm* — Lorenz & Kopf, LLP

(57) ABSTRACT

In various exemplary embodiments a hair condition determining device and a method for providing hair condition information may be provided. The device may comprise a first area and a second area configured in such a way that hairs of a user are movable between the first area and the second area, wherein in the first area at least one optical sensor for detecting light of a light source is positioned, wherein the second area includes at least one carrier, and wherein the first area and the second area are coupled by employing a connecting element in such a way that the first area and the second area face each other in such a way that a sensor main measuring direction of the at least one sensor is aligned at a predefined angle to a surface of the carrier.

19 Claims, 4 Drawing Sheets

(52) U.S. Cl.
CPC .......... *A61B 5/0059* (2013.01); *A61B 5/1032* (2013.01); *A61B 5/742* (2013.01); *A61B 2560/0238* (2013.01); *A61B 2562/0219* (2013.01); *A61B 2562/0233* (2013.01)

(58) Field of Classification Search
USPC ........................................................ 600/300
See application file for complete search history.

(56) References Cited

U.S. PATENT DOCUMENTS

| | | | |
|---|---|---|---|
| 2003/0172466 A1* | 9/2003 | Patel ........................ | A61Q 5/10 8/408 |
| 2006/0075580 A1* | 4/2006 | Chan ........................ | A61Q 5/10 8/405 |
| 2008/0260243 A1 | 10/2008 | Occelli | |
| 2008/0279804 A1* | 11/2008 | Parker ...................... | A61K 8/25 424/70.11 |
| 2010/0139682 A1* | 6/2010 | Edgar .................. | A61B 5/0071 132/202 |
| 2015/0342515 A1* | 12/2015 | Hutchings .......... | A46B 15/0038 132/148 |
| 2017/0164887 A1* | 6/2017 | Chattopadhyay .... | A42B 3/0433 |
| 2019/0285546 A1 | 9/2019 | Knuebel et al. | |

FOREIGN PATENT DOCUMENTS

| | | |
|---|---|---|
| JP | 2004198398 A | 7/2004 |
| JP | 3641370 B2 | 4/2005 |
| JP | 2005167777 A | 6/2005 |
| JP | 2005321289 A | 11/2005 |
| WO | 2017198479 A1 | 11/2017 |

\* cited by examiner

HAIR CONDITION DETERMINING DEVICE AND METHOD FOR PROVIDING HAIR CONDITION INFORMATION

CROSS-REFERENCE TO RELATED APPLICATION

This application is a U.S. National-Stage entry under 35 U.S.C. § 371 based on International Application No. PCT/EP2018/083912, filed Dec. 7, 2018, which was published under PCT Article 21(2) and which claims priority to German Application No. 10 2017 222 421.5, filed Dec. 11, 2017, which are all hereby incorporated in their entirety by reference.

TECHNICAL FIELD

The present disclosure concerns a hair condition determining device and a method of providing hair condition information.

BACKGROUND

In many areas of daily life, there has been a trend for some time towards personalized programs that can respond specifically to individual requirements and needs, for example in the nutrition or health sector, but also in the area of personalized cosmetics. This can enable a user to find specific cosmetic products and/or care instructions that are tailored to the individual needs of his or her hair, thus enabling a particularly high degree of effectiveness.

In particular, young hairdressers do not yet have sound experience in dealing with damaged hair, for example, which care product or combination of care products would be appropriate for treating damaged hair. In particular, a great deal of experience is also required to achieve a successful hair coloring experience with damaged hair and to know how hair coloring products must be mixed to achieve the desired coloring result, even with damaged hair.

When treating hair with cosmetic products, the effect of the product, e.g. the intensity of a coloring, the effectiveness of a care product or the hair reshaping effect of a permanent wave, may depend strongly on the hair condition, especially the degree of damage to the hair.

Therefore, a precise determination of a hair color and a degree of damage to the hair may be of great importance and represent important parameters for the user to (objectively) assess his hair health.

For many people who want to have healthy and well cared for hair, the moisture content of their hair is an important hair parameter.

Furthermore, there is a need for a device for the acquisition of hair condition information, which enables non-destructive measurement, especially on the living hair of a person.

Furthermore, there is a need for a device for recording hair condition information, which may be controlled intuitively with one hand of a user and which makes it easy for the user to record the hair condition information with the device.

Furthermore, there is a need for a device for the acquisition of hair condition information, which allows a simple and fast calibration of at least one sensor, which is used for the acquisition of hair condition information.

BRIEF SUMMARY

Devices and methods for detecting a hair condition of a user are provided. In an exemplary embodiment, a device for detecting the hair condition includes a first area and a second are configured to allow a user's hair to move therebetween. The first area includes at least one optical sensor for detecting light from a light source, and the second area includes a carrier. The first and second areas are coupled by a connecting element such that the first and second areas are opposite each other with a sensor main measuring direction of the at least one sensor oriented at a predefined angle to a surface of the carrier.

A method for detecting a hair condition is provided in another embodiment. The method includes the steps of moving a hair condition determining device along a user's hair at a predefined distance from the hair, and illuminating the hair with a light source. During illumination, a portion of the light that has interacted with the hair is detected with at least one first sensor. A degree of hair damage is detected utilizing a second sensor. A movement pattern of the hair condition determining device in space is detected utilizing an acceleration sensor, and an electronic circuit device processes detected hair condition information based on the detected movement pattern.

BRIEF DESCRIPTION OF THE DRAWINGS

The present disclosure will hereinafter be described in conjunction with the following drawing figures, wherein like numerals denote like elements, and wherein.

DETAILED DESCRIPTION

Figure 1:
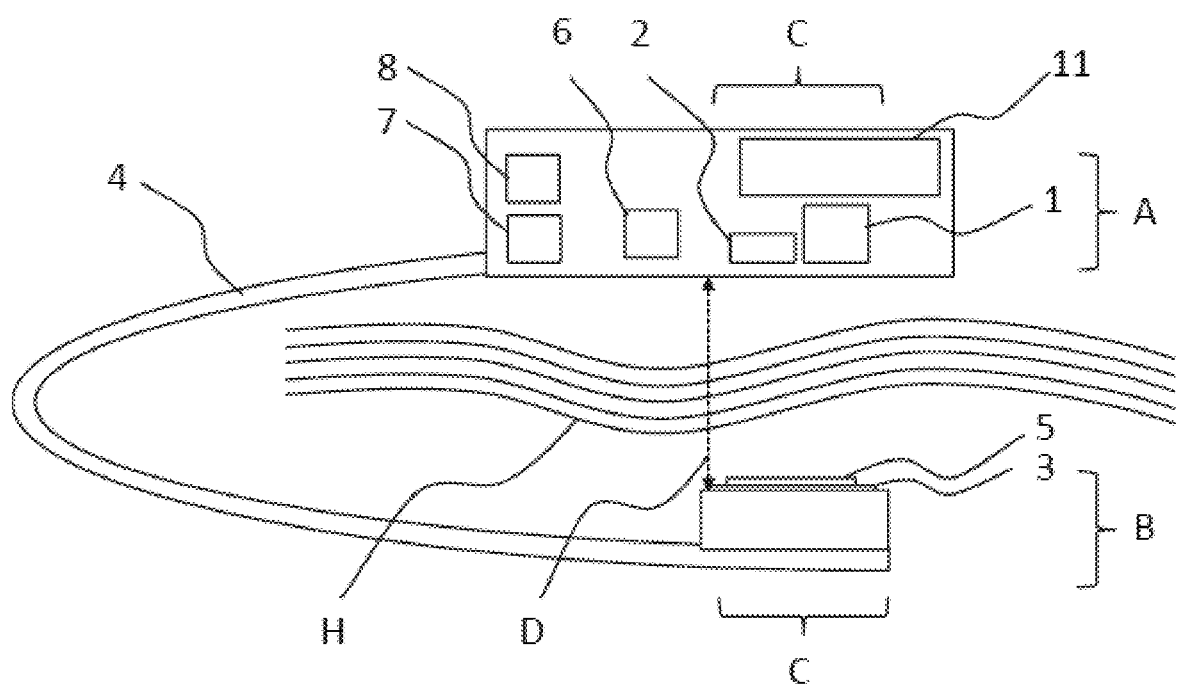
FIG. 1 is a schematic side view of a hair condition determining device for providing hair condition information according to different exemplary embodiments.

The following detailed description is merely exemplary in nature and is not intended to limit the disclosure or the application and uses of the subject matter as described herein. Furthermore, there is no intention to be bound by any theory presented in the preceding background or the following detailed description.

Damage to the hair may be caused by natural or man-made processes. The most important type of damage may be oxidative damage.

The natural processes may, for example, have a combined (e.g. simultaneous) effect of UV light and oxygen ($O_2$) on the hair.

The man-made processes may include, for example, the application of hair dyes (also known as coloration, which includes bleaching), and/or styling or reshaping of the hair (e.g. creating a perm).

In addition to desired cosmetic effects, such as a lightening of the hair, the hair may also be severely damaged, for example when using oxidizing agents.

For example, the cysteic acid content of damaged hair may be increased due to an oxidation of the amino acids cystine and cysteine to cysteic acid, which are very abundant in hair.

The oxidation of cystine/cysteine to cysteic acid can destroy the mechanical stability of the hair and even lead to complete hair breakage if used several times. However, macroscopically perceptible, e.g. tactile, properties of the hair, e.g. a surface texture, e.g. a surface roughness, may be negatively influenced even before this. Damaged hair, for example, may have a higher surface roughness than undamaged hair.

Results of cosmetic treatments may depend on other properties of the treated hair, such as hair color (especially in the case of coloring), hair structure (especially in the case of styling, e.g. perming, straightening, etc.), moisture content (in the case of a care product), etc.

In various exemplary embodiments, a hair condition determining device is provided which makes it possible to determine a user's hair condition by employing at least one optical sensor. The determination of the hair condition may be carried out in different exemplary embodiments during a brushing or picking up of hair by employing the hair condition determining device, i.e. the hair condition determining device may be set up in such a way that a guiding option for hair may be realized.

In various exemplary embodiments, successive measurements made along a hair sample may be used to determine the condition and development over a time axis, e.g. to determine an area of damage or change.

In different exemplary embodiments, a recommendation may be provided based on the determined hair condition, e.g. regarding a cosmetic hair treatment product, a composition of a hair treatment product and/or a hair treatment recommendation.

In various exemplary embodiments, a hair condition determining device and a method described herein may be provided as part of a "Smart Salon" system, which is a holistic system comprising a plurality of intelligent smart devices, which may provide identification and advice towards the provision of at least one hair treatment product to improve a user's hair condition and/or desired hair color.

An optical sensor is herein understood to be a sensor which, by employing optical elements, conducts electromagnetic radiation in the wave range of visible and invisible light, in the broader sense short-wave radiation (UV light), visible light (also abbreviated as VIS), long-wave radiation such as near infrared light (NIR) and/or infrared light (IR)), and which is detected, recorded, analyzed and further processed by employing a detector (e.g. an electronic detector, e.g. for visible light, for NIR and/or IR light, a photometer or the like), especially on the basis of spectroscopic methods for infrared radiation.

In this context, reference can be made to "the sensors", for example with regard to a data transmission between the sensors and the data processing device, a set-up of the sensors, etc. This is to be understood as meaning that the sensors may comprise a set of sensors and/or sensor circuits located in or on the body of the device, e.g. a set of optical sensor(s) (e.g. spectrometer, camera, microscope), microphone(s), speed sensor circuit(s), etc., or, where this is apparent from the context, part of the said sensors and/or sensor circuits.

In various exemplary embodiments, the optical sensor may be a near infrared (NIR) sensor, e.g. a NIR spectrometer or a NIR camera, which may be set up to detect hair damage and/or moisture content.

In various exemplary embodiments, the detection may be carried out by absorption, reflection and spectroscopy, whereby the respective methods to be carried out may be evaluated by employing a mobile or portable data processing device and/or may be evaluated by employing a network software (cloud), in order to do justice to the complexity of the spectroscopy evaluation, for example.

In various exemplary embodiments, the hair condition determining device may comprise at least one (N)IR spectrometer and/or one (N)IR/VIS spectrometer, as they are installed in the spectrometers mentioned below.

In various exemplary embodiments, for example, the "MicroNIR® OnSite" by Viavi Solutions Inc. may be provided as a suitable spectrometer in various exemplary embodiments. The spectrometer may detect and/or determine a measurement with a measurement duration in a range of about 0.10 s (seconds) to about 5 s, for example in a range of about 1 s to about 3 s, for example about 2 s, at least one recording of the near infrared and/or infrared spectra of hair of a consumer in almost real time. In various exemplary embodiments, the spectrometer may include at least one integrated vacuum tungsten lamp and an InGaAs photo diode array with 128 pixels. In various exemplary embodiments, the "MicroNIR® OnSite" may operate in a wavelength range from about 6060 $cm^{-1}$ to about 10526 $cm^{-1}$.

In various exemplary embodiments, a spectrometer "i-Spec™ Nano" by B&W Tek may be used. In various exemplary embodiments, the spectrometer may include a light source and operate in a wavelength range from about 4545 $cm^{-1}$ to about 7692 $cm^{-1}$.

In various exemplary embodiments, a NIR/VIS spectrometer "QualitySpec® Trek" by ASD Inc. may be used and in various exemplary embodiments, the spectrometer may operate in a wavelength range from about 28571 $cm^{-1}$ to about 400 $cm^{-1}$ (from about 350-2500 nm).

In various exemplary embodiments, a spectrometer may be the "SCiO™ by Consumer Physics". The spectrometer may operate in the shortwave range of the NIR at wavelengths from about 9090 $cm^{-1}$ to about 14285 $cm^{-1}$ (from about 700 to about 1100 nm).

In various exemplary embodiments, a spectrometer by Attonics Systems may be used, which may operate either in the wavelength ranges from about 9090 $cm^{-1}$ to about 26,315 $cm^{-1}$ (VIS-NIR) or from about 3333 $cm^{-1}$ to about 10,000 $cm^{-1}$ (NIR). In various exemplary embodiments, the spectrometer may be based on interferometers and may offer a high light throughput and a high spectral resolution (smaller than about 5 nm for VIS-NIR spectrometers and larger than about 20 nm for the NIR spectrometer). In various exemplary embodiments, the spectrometer may include a Multi-Phase Shift Array (MPA) chip and an optical set-up in a circular tube.

In various exemplary embodiments, the miniature spectrometers "USB2000-VIS-NIR" or "USB4000-VIS-NIR" by Ocean Optics may be used. In various exemplary embodiments, the spectrometer may operate in a wavelength range from about 350 nm to about 1000 nm.

In various exemplary embodiments, a NIR evaluation module "DLP® NIRscan" or "DLP® NIRscan Nano" by Texas Instruments may be used. In various exemplary embodiments, the evaluation module includes two tungsten lamps and InGaAs photo diodes as detectors. In various exemplary embodiments, the "DLP® NIRscan" module may operate in a wavelength range from about 4016 $cm^{-1}$ to about 7407 $cm^{-1}$ and the "DLP® NIRscan Nano" module in a range from about 5882 $cm^{-1}$ to about 11,111 $cm^{-1}$.

In various exemplary embodiments, the "NeoSpectra™" by Si-Ware Systems may be used as a further suitable NIR sensor, for example the NeoSpectra™ SW62221-1.7 sensor, the NeoSpectra™ SW62221-2.1 sensor and the NeoSpectra™ SW62221-2.5 sensor, which can operate in different wavelength ranges.

In various exemplary embodiments the optical sensor may be a sensor for visible light, e.g. a spectrometer or a camera for a spectral range of visible light, especially in a range where fluorescent light is emitted by hair. The optical sensor may be set up to detect hair damage.

The optical sensor for visible light or a further sensor for visible light, e.g. a spectrometer or a color camera, may be set up in various exemplary embodiments to determine the initial hair color of the user. In a case where the camera (or an additional camera) is provided, it may also be used to determine a hair density.

The optical sensor to detect hair damage (NIR or fluorescent light) may be provided in the hair condition determining device.

In various exemplary embodiments, a combination of several of the above mentioned sensors may be used to obtain a more comprehensive picture of the hair condition. The detection of two or more hair condition parameters may be understood as a two-dimensional or multi-dimensional measurement, which may be used to improve an analysis result regarding the hair condition.

In various exemplary embodiments, the hair condition determining device may take the desired result into account when determining the recommendation, e.g. of the hair treatment product, in such a way that the recommended product and/or hair treatment is suitable to achieve the desired result on the user's hair.

In various exemplary embodiments, another conventional input device may be provided alternatively or additionally as an input device on the hair condition determining device, e.g. keys, a touch-sensitive screen, etc. In various exemplary embodiments, the hair condition determining device may have an output device for outputting the hair condition information and/or the recommendation, e.g. a loudspeaker and/or a display, or light indicators such as LEDs in different colors or numbers, which are directly visible or illuminate a symbol/icon.

In various exemplary embodiments, the hair condition determining device may be part of a hair condition determining system which may further comprise at least one display device which may be used as an output device for the hair condition information and/or the recommendation.

For the direct or indirect determination of the hair condition and, if applicable, for the direct or indirect determination of the recommendation (e.g. of the hair treatment product and/or the hair treatment recommendation), the device or the system in various exemplary embodiments may include a data processing device.

In various exemplary embodiments, e.g. if the display device is a smartphone, tablet or similar, the display device may also be used as an input device and/or as an external data processing device.

In various exemplary embodiments, data and/or experience values of (further) users who may have a similar hair condition (e.g. a similar degree of damage and/or a similar hair color) and possibly a similar profile (age, gender, lifestyle, hair type, etc.) may be taken into account when determining the recommendation. A broad set of data and/or experience may be used to optimize the result. The system may be designed as a learning system.

In various exemplary embodiments, the hair condition determining device may be configured to transmit a current hair damage condition, which may have been detected by employing the NIR sensor, for example, and a current hair color of a user, by employing visible light or UV light measurement, for example, which may have been detected by employing the color sensor, from the hair condition determining device to a hair treatment product mixing device, which may determine an individual hair treatment product composition and provide the user with a corresponding hair treatment product, for example a shampoo or a cure.

In various exemplary embodiments a standardized and objective evaluation of the treatment result may be made possible using the hair condition determining device. For this purpose, the optical sensor included in the device and possibly other sensors may be used to determine the hair condition of a consumer after following the recommendation, e.g. after applying the recommended product and/or after carrying out the recommended treatment.

This enables continuous and, if necessary, frequent measurements of reliable hair damage values and may enable the user or the consumer to monitor the health and/or care status of their hair over time and to be strengthened in their belief that the treatment will be successful.

In various exemplary embodiments, the hair condition determining device may be set up in such a way that the optical sensor may be used to precisely determine the degree of oxidative hair damage by determining a cysteic acid content. The optical sensor may be set up to take one or more images in a near infrared (NIR) range.

In various exemplary embodiments the optical sensor may be a VIS sensor, which may determine hair damage by employing fluorescence.

In various exemplary embodiments, the near infrared range may be a wavelength range in which damaged hair has absorption structures, e.g. in which cysteic acid absorbs light.

Undamaged hair may typically contain cysteic acid in a range of about 0.5% to about 1% (by weight). In the presence of damage, for example as a result of multiple ultra-bleaching and/or other damage mechanisms, the cysteic acid content may rise to over about 15% (by weight).

In various exemplary embodiments, this property is used to quantify the degree of damage to the hair as a cysteic acid content.

In various exemplary embodiments, damaged hair may show an inherent fluorescence, which is used to determine the degree of damage by measuring the fluorescence intensity of the hair.

In various exemplary embodiments, the hair may be exposed to UV light (e.g. light in a wavelength range from about 315 nm to about 380 nm) using the light source to determine the fluorescence intensity of the hair. For this purpose, the sensor device may be equipped with a UV light source. The UV light source may be a UV LED or another suitable light source which is small enough to be accommodated in the device and/or in the first area of the device.

During exposure, fluorescent light emitted by the hair may be registered. The fluorescence intensity may be determined from the registered light. The degree of damage to the hair may then be determined by taking into account the fluorescence intensity of the hair.

Accordingly, the optical sensor may be sensitive at least in the fluorescence wavelength range. The optical sensor may include or be a camera, a photometer, a colorimeter and/or a spectrometer. In various exemplary embodiments, a filter may be placed between the hair and the optical sensor.

Thanks to technological progress in recent years, optical sensors (for the visible wavelength range or for the NIR or IR range) can now be provided which are small enough to be accommodated in an enclosure of the device.

In various exemplary embodiments, e.g. in a case where the optical sensor, e.g. a detector of the optical sensor and/or optical components like a dispersing element of a spectrometer or similar, requires more space than is available near the hair, at least one light guide device may be provided. The space-requiring component (e.g. the light source and/or the detector) may be positioned at a part of the hair condition determining device which provides more space, and the at least one light guide device may be designed to guide light (e.g. the light for illuminating the hair or the light which has interacted with the hair) between the component and an entry or exit point of the light on the enclosure of the device. Conventional structures known for this purpose, e.g. optical fibers, optical channels, mirrors and/or other optical elements, etc., may be used as light guide devices, whereby it must be ensured that any light-transmitting material used is light-transmitting for the wavelength range to be guided, e.g. in the case of NIR light for the NIR wavelength range up to about 2.5 μm.

In various exemplary embodiments, the near infrared (NIR) and/or infrared (IR) spectrum may be obtained, for example, by employing ATR (near) infrared spectroscopy ("Attenuated Total Reflection"). By applying mathematical models, a mathematical model may be created by measuring calibration hair samples, which have a cysteic acid content determined by a known analytical method.

When analyzing an NIR or IR spectrum, or at least part of it, recorded on the hair of a consumer or a user, the model may be used to calculate the cysteic acid content of various exemplary embodiments, and thus the hair damage. An analysis of at least a part of the spectrum and an application of the model may be carried out by employing the data processing device, for example (with suitable apps) by employing known smartphones, tablets or similar.

The light source in various exemplary embodiments may be an NIR light source or/and an IR light source for exposing the hair to NIR or IR light.

The determination of the degree of damage to hair may be carried out according to various exemplary embodiments either by using the near-infrared range, i.e. by irradiating the hair with the near-infrared light and spectral analysis of at least part of the NIR light after it has interacted with the hair, or by using the infrared range, i.e. by using the infrared light by irradiating the hair with infrared light and spectral analysis of at least part of the IR light after it has interacted with the hair, or using both the near infrared and infrared ranges, i.e. by irradiating the hair with near infrared and infrared light and spectral analysis of at least part of the NIR and at least part of the IR light after it has interacted with the hair.

In various exemplary embodiments, a measured near-infrared (NIR) range may show wavelengths from about 12,500 $cm^{-1}$ to about 4000 $cm^{-1}$, e.g. from about 5022 $cm^{-1}$ to about 4020 $cm^{-1}$. This wavelength range may show characteristic overtone and combination oscillations of e.g. CH, OH and NH groups.

In various exemplary embodiments, at least part of the near infrared and/or infrared light may show an (infrared) wave number range from about 1100 $cm^{-1}$ to about 1000 $cm^{-1}$, e.g. about 1040 $cm^{-1}$. Among other things, the relevant absorption bands of the component to be analyzed, cysteic acid may be found here.

In various exemplary embodiments, a calibration model may be created using the results of a quantitative computer-assisted evaluation (also referred to as chemometric analysis) for a plurality of calibration hair samples in combination with values for a cysteic acid content of the respective calibration hair sample obtained by an independent method, e.g. by high-pressure liquid chromatography, for the same calibration hair samples.

Once the calibration model is available, the concentration of cysteic acid (as a measure of hair damage) may be calculated very easily for the hair to be measured in various exemplary embodiments from the spectra in comparison with the calibration spectra, using the (N)IR spectrum recorded for the hair.

In various exemplary embodiments, suitable mathematical models of predictive analytics may be used to quantify the cysteic acid content (e.g. by fluorescence analysis and/or (N)IR spectroscopy) or the degree of damage.

In various exemplary embodiments, a method is provided which is simple in use and which enables a precise determination of the degree of oxidative damage to hair by employing fluorescence detection and/or by detection of absorption and methods from predictive analysis.

In various exemplary embodiments, a mobile or portable data processing device may be used to provide the determined hair conditions or the recommendation. As a portable data processing device, a smartphone, an iPad®, a tablet or laptop may be used.

In various exemplary embodiments, a method may be provided which, by employing a simple image analytical method, which can be determined for example by using a simple device (e.g. a UV LED, a white light, NIR and/or IR illuminating device, a filter, a portable NIR sensor, a portable (NIR and/or VIS) spectrometer, possibly in connection with a mobile data processing device (e.g. a smartphone or tablet) and, if applicable, a predictive analytics method, provides information regarding a user's hair condition and, if applicable, a recommendation based thereon.

According to various exemplary embodiments, predictive analytics may use at least one method from a group of methods, the group of methods comprising linear or multi-linear regression, polynomial regression, neural network method, support vector machine method, decision trees method ("decision trees", "random forest", "tree ensembles") and other methods.

By using an acceleration sensor, it may be possible in various exemplary embodiments, to determine a position of the hair condition determining device. For example, an acceleration sensor may be used to determine the beginning and/or end of a hair condition detection process. Assuming that a hair condition detection process typically starts at the hairline and ends at the hair tips, a spatially resolved determination, e.g. hairline/middle area/tips, of the hair condition information, hair color and associated hair damage may be possible, possibly in combination with a speed determined by employing the acceleration sensor at which the hair condition determining device is moved.

In the context of this application, the accelerometer feature may include a 'classical' motion sensor or a gyroscopic sensor.

Data transmission from the hair condition determining device to an external data processing device and/or to an external storage device may be done in various exemplary embodiments via cable or via known radio data transmission standards (e.g. Bluetooth, Bluetooth Low Energy (BLE), WLAN, Wi-Fi, NFC, etc.).

In various exemplary embodiments, the hair condition determining device for providing hair condition information may include a first area and a second area configured in such a way that hair of a user is movable between the first area and the second area, wherein in the first area at least one optical sensor for detecting light of a light source is located.

The hair condition determining device is configured in such a way that the hair of a user is movable between the first area and the second area, wherein the second area comprises at least one carrier, and wherein the first area and the second area are coupled by employing a connecting element such that the first area and the second area face each other such that a main sensor measuring direction of the at least one sensor is oriented at a predefined angle to a surface of the carrier.

In various exemplary embodiments, the hair condition determining device may be operated by a user with one hand. With one hand, the user may expose at least one hair or strand of hair and hold the hair under a tensile load on the exposed hair, which is even more comfortable for the customer, and with the other hand guide the hair condition determining device along the exposed hair.

In various exemplary embodiments, the user may move the hair condition determining device with one hand according to a predefined pattern of movement in space in order to control at least one action of the hair condition determining device with one hand, e.g. to perform a storage process of a just measured hair color and/or a just measured degree of hair damage, for example to perform an erasure process of a hair color and/or a degree of hair damage which has just been determined and/or stored in a storage device and/or a degree of hair damage which has just been determined and/or stored in a storage device, for example to perform a data transmission process of a hair color and/or a degree of hair damage which has just been determined and/or stored in a storage device from the hair condition determining device to an external data processing device.

In various exemplary embodiments, an electronic circuit device may be set up to detect by employing an acceleration sensor whether a hair condition determining device has not been used for a long period of time and then to put the hair condition determining device into a standby mode.

In various exemplary embodiments, an electronic circuit device may be configured to detect by employing an acceleration sensor whether a hair condition determining device has not been used for a prolonged period of time and is currently being used and then to set the hair condition determining device into an active mode. In various exemplary embodiments, for example, depending on the frequency of movement of the hair condition determining device, switching off the color sensor and/or the hair damage sensor may be realized by employing a circuit device in order to reduce the power consumption of the hair condition determining device in a standby mode.

In various exemplary embodiments, the connecting element may comprise an elastic material. In various exemplary embodiments the elastic material is exemplified by the fact that it is repeatedly deformable when a force is applied and returns to its original initial state when the force is removed.

In various exemplary embodiments, the connecting element may have a thickness or material thickness in a range from about 2 mm to about 20 mm.

In various exemplary embodiments, the connecting element may comprise a bent flat steel with a width in a range of about 5 mm to about 30 mm.

In various exemplary embodiments, the connecting element may comprise a spring steel, for example X10CrNi18-8,38Si7, 61SiCr7, 52CrMoV4, 51CrV4, C67E/C67S or other spring steels known to the expert for such applications.

In various exemplary embodiments, the connecting element may include a stainless spring steel.

In various exemplary embodiments, the elastic connecting material may be designed with a matte and/or matte coated finish, which may allow a light emitted by a light source to be reflected only slightly or in a predefined range and minimize a negative influence on at least one sensor.

In various exemplary embodiments, the connecting element may have a U-shaped configuration and the first area and the second area may each be positioned at an end area of the U-shaped configuration.

In various exemplary embodiments, the connecting element may comprise a stop limitation near and/or adjacent to the second area, the stop limitation being designed so that, if the connecting element is compressed by employing hand muscle force, excessive force loading by the carrier and/or the calibration material on a sensor front side may be avoided.

In various exemplary embodiments, at least one calibration medium may be located on an area of the surface of the carrier facing the first area, the calibration medium being configured to calibrate at least one sensor of the device.

In various exemplary embodiments, the design of the device may allow the calibration medium to be part of the device and thus no additional calibration medium is required for at least one calibration procedure.

In various exemplary embodiments, it may be possible that the calibration medium is already attached to the device so as to prevent a calibration medium not being available when the device is used in mobile applications, so that calibration would not be possible. In various exemplary embodiments, it may be possible to ensure that a calibration medium that is physically connected to the device is available at any location where the device is to be calibrated and that no external calibration medium is required.

In various exemplary embodiments, the calibration medium or a surface of the calibration medium may be positioned perpendicularly or at a predefined angle to a main measuring direction of the at least one sensor when performing a calibration. In various exemplary embodiments, the predefined angle may be in a range from about 70 degrees to about 110 degrees, for example in a range from about 85 degrees to about 95 degrees.

In various exemplary embodiments, a lateral distance of a vertical central axis of the calibration medium to a vertical central axis or longitudinal axis of at least one sensor may lie in a predefined range, for example in a range from about 20 mm to 0 mm, for example in a range from about 10 mm to 0 mm.

In various exemplary embodiments, the calibration medium may be used as a reference calibration medium to calibrate the color sensor and/or the hair condition sensor.

In various exemplary embodiments, a material of the carrier and/or the ceramic may be kept in the color white or in a white shade to allow a high reflection of light. In various exemplary embodiments, the ceramic material or the ceramic substance may comprise a glass ceramic and/or leucite-reinforced glass ceramic. In various exemplary embodiments, a leucite-reinforced glass-ceramic may comprise a glass phase and a leucite-type crystal phase. In various exemplary embodiments, the material may be based, for example, on the three-component system $SiO_2$, $Al_2O_3$ and $K_2O$.

In various exemplary embodiments, the ceramic material used may be for example ALOTEC® 92. In various exemplary embodiments, ALOTEC® 92 may be used with an $Al_2O_3$ content of greater than or equal to about 92 mass %, a density of greater than about 3.64 g/cm³, an open porosity of about 0 vol %, a modulus of elasticity of greater than about 300, a bending stiffness (four-point) of greater than about 320 MPa, a Weibull modulus of about 14 m, a fracture toughness of about 3 to about 4 MPam$^{1/2}$, a hardness of greater than about 12 HV(1), a coefficient of thermal expansion of about 7.5 $10^{-6}K^{-1}$, a roughness "as fired" of about 1.9 µm and a roughness "polished" of about 0.3 µm. It goes without saying, however, that other suitable ceramic materials may be used instead of ALOTEC® 92.

In various exemplary embodiments, when producing a glass-ceramic starting from viscous glass, the form may first be produced and in a subsequent tempering step, i.e. a method for increasing the stability of the ceramic, the previously amorphous volume may be crystallized in a targeted manner by the targeted use of temperature changes. Such systems are exemplified by high mechanical strength and good thermal shock resistance. In various exemplary embodiments it is possible to combine the positive optical properties of glass with the positive mechanical properties of ceramics by using a leucite-reinforced glass-ceramic as calibration medium.

In various exemplary embodiments, the NIR sensor may be set to a calibration mode during a calibration process using the calibration medium after the NIR sensor has been activated. In various exemplary embodiments, the calibration medium may then be brought to the NIR sensor at a predefined distance from the NIR sensor. In various exemplary embodiments, the calibration medium may be positioned directly in front of or directly against a main measuring surface of the color sensor and/or the NIR sensor during a calibration process of the NIR sensor. In various exemplary embodiments, the NIR sensor may then irradiate the calibration medium, for example a ceramic, by employing an infrared source (IR source) and measure a reflection (and thus also an absorption) of the reflected infrared rays. In various exemplary embodiments the NIR sensor may then generate an internal calibration profile for all further measurements.

In various exemplary embodiments, the color sensor may include a self-calibrating sensor. In various exemplary embodiments, the color sensor may optionally be calibrated using the calibration medium.

In various exemplary embodiments, the color sensor may be set to a calibration mode during a calibration process using the calibration medium after the color sensor has been activated. In various exemplary embodiments, the calibration medium may then be positioned at a predefined distance from the color sensor, e.g. by using the user's muscle power. In various exemplary embodiments, the calibration medium may be positioned directly in front of or directly against a main measuring surface of the color sensor during a calibration process of the color sensor. In various exemplary embodiments, the color sensor may then irradiate the calibration medium, for example a ceramic, by employing an infrared source (IR source) and measure a reflection of the reflected light rays. In various exemplary embodiments, the color sensor may then generate an internal calibration profile for all further measurements. In various exemplary embodiments, a calibration of a self-calibrating color sensor may be necessary as an option for better calibration of the light source for particularly precise measurements.

In various exemplary embodiments a calibration procedure may be simplified by using the calibration medium as part of the device.

In various exemplary embodiments, the calibration medium or the carrier may also be set up as a clamping device and/or guiding aid, so that a consumer's hair may be guided in the direction of the measuring sensors. In other words, in various exemplary embodiments, the carrier and/or the calibration medium may be guided towards the at least one sensor by employing a user's hand muscle force in order to be able to perform a measurement at the at least one sensor at a predefined distance, for example in a range from about 0 mm to about 10 mm, for example in a range from about 2 mm to about 8 mm, for example in a range of about 3 mm, between the carrier or the calibration medium and the at least one sensor.

In various exemplary embodiments, the calibration medium may be or include a ceramic material.

In various exemplary embodiments it may be possible to use the ceramic to maintain a constant background behind the hairs of a consumer, so that repeatable or reproducible measurements may be achieved with the hair condition determining device.

In various exemplary embodiments, the calibration medium may be a ceramic plate which is applied to a carrier.

In various exemplary embodiments, the first area may comprise a color sensor for detecting a user's hair color and/or hair damage via UV light by employing absorption or reflection and a hair condition sensor for detecting a user's hair condition, wherein the color sensor detects a user's hair color at a first time and the hair condition sensor detects a degree of hair damage and/or hair moisture content of the user at a second time, and wherein the first time and the second time lie in a predefined time range.

In various exemplary embodiments, the first range may further comprise a haptic signal generator (vibrator).

In various exemplary embodiments, the color sensor may be configured to detect a user's current hair color.

In various exemplary embodiments the color sensor may be a high-end multi-band sensor or color sensor with high bandwidth or a multi-spectral color sensor.

In various exemplary embodiments, a color sensor with high bandwidth and/or extended wave spectrum for detection may be set up to provide additional color information in addition to the color spectrum perceived by the human eye for further analysis and calculation of care and coloration products.

In various exemplary embodiments, a multi-channel color measurement with transformation into a representation space, for example a CIE LAB or into other representation spaces known to the expert, may be realized by employing the color sensor.

In various exemplary embodiments, an L*a*b* color space may be understood as a color space containing all colors in a device-independent form. By employing a transfer of color values into the L*a*b* color space, the loss-free conversion of color information from one color system to another, from one type of device to another, may therefore be realized in various exemplary embodiments.

In various exemplary embodiments, the predefined time range may be in the range of about 10 ms (milliseconds) to about 1000 ms, for example. In various exemplary embodiments, the first time may be in a range of about 20 ms to about 50 ms and the second time in a range of about 50 ms to about 250 ms and vice versa. In various exemplary embodiments, a measurement may be carried out by employing the hair condition sensor and shortly afterwards by employing the color sensor. In various exemplary embodiments, the measurements may be carried out so closely one after the other that they may be performed at approximately the same time.

In various exemplary embodiments, a first measured result may be processed with the color sensor and a second measured result with the hair condition sensor and/or a third measured result with the acceleration sensor at least jointly in one cycle, for example a storage cycle of the electronic circuit device, and/or may be combined to form a data package which may be stored, for example by employing the circuit device, in the storage device of the hair condition determining device and/or in an external storage device and/or in an external data processing device by employing a wireless connection.

In various exemplary embodiments, the color sensor may be set up to detect a current hair color of a consumer.

In various exemplary embodiments, the first area or the second area may further comprise an acceleration sensor.

In various exemplary embodiments, the term acceleration sensor may refer to an acceleration meter, accelerometer, B-meter or G-sensor.

In various exemplary embodiments, the acceleration may be measured or indicated in the SI unit $m \cdot s^{-2}$ (meter per second squared).

In various exemplary embodiments, the acceleration sensor may be set up to detect a movement and/or a speed of a forward movement of the hair condition determining device by one user.

In various exemplary embodiments, the acceleration sensor may be configured to detect a movement and/or a speed of a forward movement of the hair condition determining device by a user, for example when different hair areas of the hair are measured by employing the hair condition determining device, to detect an instantaneous position of the hair condition determining device with respect to the hair, for example with respect to a hair beginning or a hair end, and/or to detect a direction of movement and/or a speed of movement of the hair condition determining device.

In various exemplary embodiments, the accelerometer may be set up to detect a movement condition of the device in space. In various exemplary embodiments, the use of an acceleration sensor in addition to other sensors, for example a color sensor and a hair condition sensor, allows the hair condition determining device to be operated with one hand by controlling the operation of the hair condition determining device by employing a physical movement and gesture control.

In various exemplary embodiments, the acceleration sensor may be set up to detect a predefined "back and forth" movement and/or swivel movement and/or "shake" movement and/or "shake out" movement and/or "point" movement of the hair condition determining device and/or compare it with a predefined movement pattern and/or assign a movement to a known movement pattern.

In various exemplary embodiments, after picking up the device and removing the device from a charging station and then holding the device upright, the acceleration sensor may be set up to detect the vertical alignment of the device, wherein a circuit device is set up to compare the measurement result with predefined known movement patterns based on at least one measurement result of the acceleration sensor and to determine a predefined movement pattern corresponding to the movement and to switch on or wake up the device.

In various exemplary embodiments, when the device is held vertically and the device is shaken, the acceleration sensor may be set up to detect the vertical alignment of the device and the shaking, wherein a circuit device may be set up to compare the measurement result with predefined known movement patterns based on at least one measurement result of the acceleration sensor and to determine a predefined movement pattern corresponding to the movement and to activate or start a new measurement series based on the determined predefined movement pattern.

In various exemplary embodiments, when the device is shaken out, the accelerometer may be set up to detect the shaking as a movement pattern, with a circuit device being set up, based on the detected movement pattern employing the acceleration sensor, to compare the movement pattern with predefined known movement patterns and determine a predefined movement pattern corresponding to the movement and, based on the determined predefined movement pattern, delete a last measurement or a last series of measurements from a storage device, for example from a storage device of the hair condition determining device and/or from a storage device of an external data processing device and/or from an external database.

In various exemplary embodiments, the device may be set up to carry out simultaneous measurements by employing an NIR sensor and a color sensor and/or a motion sensor, or to simultaneously store corresponding measurement values, so that a respective detected color of hair and/or a position on the hair may be clearly assigned to a detected degree of hair damage and archived in a storage device. In various exemplary embodiments, a position on the hair may comprise an upper area at the hairline, a middle area and a lower area, or a border area. In various exemplary embodiments, for example, an upper area of a user's hair at the hairline may have a brown tone with a low to slight degree of damage to the hair, and a lower border area of a user's hair may have a light blonde tone at the tips with a medium to severe degree of hair damage.

In various exemplary embodiments, simultaneous measurement by employing an NIR sensor and a color sensor and/or the detection of a movement of the device by employing the movement sensor may allow for a quick operation of the device by consecutive measurement runs.

In various exemplary embodiments, simultaneous measurement by employing an NIR sensor and a color sensor and/or detection of a movement of the device by employing the movement sensor may allow infrared measurement by employing the NIR sensor and measurement of the visible light by employing the color sensor to be clearly assigned to a position on the hair of a consumer.

In various exemplary embodiments, simultaneous measurement by employing an NIR sensor and a color sensor and/or detection of a movement of the device by employing the movement sensor may allow localized measurement zones with simultaneous determination of infrared value and color value to be realized in order to document the historical damage or change of the hair on the basis of several measurements of the hair.

In various exemplary embodiments, a miniaturized piezoelectric accelerometer made of silicon may be used as an acceleration sensor, which is able to convert the pressure fluctuations caused by acceleration, i.e. by the acceleration of the hair condition determining device with a hand movement, into electrical signals.

In various exemplary embodiments, an acceleration sensor may be used, for example, a piezoresistive or piezocapacitive or micro-mechanical gyroscopic sensor, which provides a signal that can show the acceleration as well as the inclination of the sensor (position in relation to gravity).

In various exemplary embodiments, for example, a piezoceramic sensor plate may convert dynamic pressure fluctuations into electrical signals, which may be further processed accordingly. The pressure fluctuations are generated by a (seismic) mass attached to the piezoceramic and can act on the piezoceramic when the entire system is accelerated.

In various exemplary embodiments, Micro-Electro-Mechanical Systems (MEMS) may be used as acceleration sensors, which may be made of silicon. In various exemplary embodiments, the sensors may represent spring-mass systems, in which the springs may be bars of silicon only a few μm wide and the mass may also be made of silicon. Due to the deflection during acceleration, a change in electrical capacitance may be measured between the spring-mounted part and a fixed reference electrode. The entire measuring range may correspond to a change in capacitance of about 1 pF. The electronics for evaluating this small capacitance change may be accommodated on an integrated circuit (IC).

In various exemplary embodiments, the accelerometer may be set up in such a way that, when the sensor signal is horizontal or vertical, the DC components of the sensor signal differ, so that the position of the body, for example the hair condition determining device, may also be determined in space.

In various exemplary embodiments, since an acceleration sensor can only react with maximum sensitivity in one dimension, it may be necessary to combine a plurality of sensors, for example two or three sensors, in order to be able to detect movements in the plane or in three-dimensional space. In various exemplary embodiments a plurality of sensors may be used to measure human motion behavior in the three spatial dimensions (planes) more precisely.

In various exemplary embodiments, the accelerometer may be set up to detect translational and rotational motion and a mixture of both at a predefined sampling rate.

In various exemplary embodiments, an activity or pattern recognition method may include several successive processing steps. In various exemplary embodiments, processing of measurement data acquired by employing the acceleration sensor may include the acquisition of the raw sensor data, their preprocessing and segmentation, the acquisition of meaningful characteristics and the actual classification, which may assign the recorded data to the individual activities. In various exemplary embodiments, it may be the objective to determine from a set of activities or motion sequences the motion sequence that can best explain the measured sensor data. In various exemplary embodiments, a measuring range of about ±5 G, for example about ±4 G, and a sampling rate in a range of about 20 to about 60 Hz, for example about 50 Hz, may be selected for a motion detection.

In various exemplary embodiments, the accelerometer may already be digital and to a certain degree "smart", so that most of the preprocessing steps may be performed directly on the hardware itself, e.g. analog-to-digital conversion, calibration or temperature compensation. In various exemplary embodiments, it may be useful to convert the measured raw sensor data into standardized units, e.g. m/s$^2$ or rad/s, and into coordinate systems. In various exemplary embodiments, if several sensors are used, the data streams may also be synchronized. In various exemplary embodiments this may not only concern a static offset between the signals, but may require a complete re-sampling for different sampling rates.

In various exemplary embodiments, the at least one accelerometer may provide a continuous data stream. In order to find out in which period of time which movement or activity took place, individual segments may be extracted from the stream in various embodiments. Thus, in various exemplary embodiments, it may be tried to already detect a beginning and an end of possible activities—for example by determining the intensity of the movement—or additional sensors or context information may be used. In various exemplary embodiments, a window of fixed size may be moved across the data in certain increments and/or overlapping (sliding window). In various exemplary embodiments it is important to ensure that the segment size is not too small, but also not too big. If it is too small, concise movement patterns could be cut off. If it is too big, patterns of several successive movements could blur. In various exemplary embodiments, the measurements may be weighted additionally according to their position in the segment, for example as a Hamming window. In various exemplary embodiments, a sliding window with a size of about 128 samples, for example at about 50 Hz, may be used for approx. 2.56 s with rectangular windows (unweighted), which may be slid over each other with half overlap. In various exemplary embodiments, for example, a ring buffer may be used, which may be filled first and then all samples may be read out and further processed.

In various exemplary embodiments, the calculation and selection of features may be carried out in such a way that meaningful features may be calculated from the output signals measured by the sensors. Features may then be calculated for each segment and passed on to a classification procedure as a feature vector. The space spanned by the feature vectors may be called feature space. The more features are calculated per segment, the larger or higher-dimensional the feature space may be. For feature selection and reduction, automatic heuristics and methods such as principal component analysis may be available in various exemplary embodiments. Established features may include statistical moments such as mean value, variance, inclination and curvature. Frequency-based features may be realized using FFT, such as peak or energy in frequency bands, body model parameters such as joint angles and orientations or even more abstract variants.

In various exemplary embodiments, the recognition of human motion may be realized by simple ad hoc composed control systems using String Matching and Dynamic Time Warping method (DTW) from voice recognition, Conditional Random Fields (CRF), time-based probabilistic models like Hidden Markov Models (HMM), Dynamic Bayesian Networks (DBN) or Computational State Space Models (CSSM). In various exemplary embodiments, discriminative statistical machine learning methods, such as Support Vector Machines (SVM) and C4.5 decision trees, may be used to detect simple movements.

In various exemplary embodiments, the device may also include an electronic circuit device, such as a processor.

In various exemplary embodiments, the circuit device may at least be configured to control an operating condition of the device based on at least one movement condition of the device detected by the accelerometer.

In various exemplary embodiments, the circuit device may also be set up to store at least one hair condition information detected by employing the at least one sensor in a storage device of the device or in an external storage device, and/or to delete at least one hair condition information from the storage device of the device or from the external storage device, and/or to transmit the hair condition information to an external data processing device, and/or to display information based on the hair condition information on a display device of the device and/or on a display device of the external data processing device.

In various exemplary embodiments, the device may further comprise a display device for displaying information based on the at least one hair condition information acquired by employing the device.

In various exemplary embodiments, the device may further comprise a vibration unit for haptically communicating the completion of a measurement, error conditions or further system conditions to the user.

In various exemplary embodiments, an input device may be used to enter a desired result, for example a desired hair color, a desired care condition or a desired styling. In addition, the input device may be used to provide the hair condition determining device with further information that may be taken into account when determining the recommendation, e.g. whether a product should be waterproof, age and/or gender of the user (e.g. in case a care product is scented), etc.

In various exemplary embodiments, the sensors may be operated simultaneously.

In various exemplary embodiments, the hair condition sensor may comprise an infrared sensor (IR sensor) or a near infrared spectroscopy sensor (NIR sensor) and/or a UV/fluorescence sensor and/or a sensor by employing which visible light may be detected.

In various exemplary embodiments, internal hair damage and/or a moisture level of the hair may be detected by employing the hair condition sensor and determined by an electronic circuit device.

In various exemplary embodiments the hair condition determining device may be part of an ecosystem of devices and/or software products. Such an ecosystem may comprise, for example, a mixing device for the production of individual hair treatment products, a separate display device, for example in the form of a "smart mirror", a central control software, which is installed on a data processing device, for example a tablet, and controls the individual devices and data flows.

In various exemplary embodiments, data recorded by the hair condition determining device as part of an ecosystem and, if necessary, further data entered by a specialist, for example a hairdresser, via an app or other suitable software, for example relating to the appearance and/or haptics of hair of at least one user, may be processed in a "cloud", whereby in particular a determination of hair damage may be processed.

In various exemplary embodiments, the concrete composition of a hair treatment product, for example a shampoo, a cure or a colorant, may be calculated based on the determined hair condition. In various exemplary embodiments, the composition of a hair treatment product adapted to the determined hair condition of the user may be determined and forwarded to the mixing device. In the mixing device, for example, the individual hair treatment product may be produced from several basic formulations. In different embodiments, the ecosystem may be controlled by a central data processing device, for example a tablet, iPad® etc. In various exemplary embodiments, the results, for example, a degree of hair damage, a moisture content, and/or a calculated hair color, may be visualized in parallel by a display device, for example a smart mirror, a user or a customer.

In various exemplary embodiments, an individual hair treatment product may be produced for a user by employing the data recorded by the hair condition determining device and/or the determined hair condition.

In various exemplary embodiments, a method for providing hair condition information may be provided. The method may include moving a hair condition determining device according to any one of Claims 1 to 14 along an area of a user's hair at a predefined distance from the hair, illuminating the hair by employing at least one light source, during illumination, detecting a portion of light that has interacted with the hair by employing at least one first sensor, detecting at least one degree of hair damage by employing a second sensor, detecting at least one movement pattern when the hair condition determining device moves in space by employing an acceleration sensor, and processing the at least one detected hair condition information based on the detected movement pattern by employing an electronic circuit device.

In various exemplary embodiments, processing may comprise at least one of the following: storing the hair condition information detected by at least one sensor in a storage device upon detection of a first movement pattern, deleting at least one hair condition information stored in the storage device and/or in the external storage device upon detection of a second movement pattern, transmitting the hair condition information to an external data processing device and/or to an external storage device upon detection of a third movement pattern, and displaying information based on the hair condition information on a display device of the device and/or on a display device of the external data processing device upon detection of a fourth movement pattern.

In various exemplary embodiments, the method may further comprise: performing the hair color detection at a first time and performing the hair damage degree detection at a second time, wherein the first time and the second time are within a predefined time range.

In other words, in various exemplary embodiments, performing the hair color detection and performing the hair damage degree detection may be performed approximately simultaneously. In various exemplary embodiments, this may allow a data set to include a hair color value (detected by the color sensor), a hair damage degree value (detected by the hair condition sensor) and a position in space (detected by the acceleration sensor). In various exemplary embodiments it is possible to provide a multi-dimensional data set by employing the hair condition determining device for further processing, e.g. for display on a display device.

In various exemplary embodiments, detecting the movement pattern may comprise comparing the detected movement with a predefined movement pattern by employing an electronic circuit device, and assigning the movement to a predefined movement pattern by employing the circuit device.

In various exemplary embodiments, the method may further comprise calibrating at least one sensor of the plurality of sensors by employing a calibration medium, wherein the hair condition determining device comprises the calibration medium, wherein the at least one sensor of the plurality of sensors is positioned opposite the calibration medium, and wherein a sensor main measurement direction of the at least one sensor of the plurality of sensors is positioned at a predetermined angle to the calibration medium, and wherein the calibration medium comprises a ceramic material.

In various exemplary embodiments, calibration may further comprise merging a first area and a second area of the hair condition determining device, such that the first area and the second area face each other at a predefined distance, wherein in the first area the first sensor and the second sensor are positioned and in the second area the calibration medium is positioned, and performing calibration of at least one sensor of the plurality of sensors during merging.

In various exemplary embodiments, a hair condition determining device, which is in a standby state (e.g. only the motion sensor and the circuit device are supplied with power), may be picked up by a user with one hand. In various exemplary embodiments, the hair condition determining device may detect a change in movement of the hair condition determining device by employing at least one acceleration sensor and transmit sensor output measurement data corresponding to the detected movement to an electronic circuit device, either wirelessly or wired. In various exemplary embodiments, the circuit device may compare the received measurement data with known motion measurement data and assign them to at least one known motion measurement data set. In various exemplary embodiments, the circuit device may activate the hair condition determining device in standby mode to an operating mode (for example, in addition to the motion sensor and the circuit device, at least one light source and at least one color sensor and one hair condition sensor are also supplied with energy from a rechargeable battery). In various exemplary embodiments, the user may move the hair condition determining device according to a predefined movement pattern before performing a series of measurements in order to achieve an operating mode of the hair condition determining device, e.g. "holding the hair condition determining device vertical" after removing the hair condition determining device from an external charging station, "holding the hair condition determining device vertical and shaking" in order to start a new series of measurements, "shaking the hair condition determining device out" in order to delete a last measurement, etc.

In various exemplary embodiments, the hair condition determining device may detect further movement patterns of the user and process corresponding commands. In various exemplary embodiments, the hair condition determining device may be set up so that it can detect new movement patterns provided by the user, i.e. movements in which the user moves his arm with the hair condition determining device in a predefined manner or repeatedly moves it in a predefined manner, and store them and assign them to specific actions or measurement sequences that may be performed by the hair condition determining device.

In various exemplary embodiments, the hair condition determining device may be activated by "holding the hair condition determining device vertical and shaking it" before a new measurement series is carried out. In various exemplary embodiments, the hair condition determining device may be parameterized in such a way that it is ready for the start of a new measurement series, e.g. the color sensor and/or the hair condition sensor and/or at least one light source on the hair condition determining device is activated. In various exemplary embodiments, the user may bring or put or move the hair condition determining device on the hair of a consumer in such a way that the hair may be located between a first area, which may, for example, comprise at least one sensor and/or one light source, and a second area, which may comprise at least one carrier and/or one calibration medium, and may be grasped by the first and the second area in a pincer-like manner by employing manual force of the user without causing damage to the hair.

In various exemplary embodiments, a hair condition measurement may be carried out at one point by employing the hair condition determining device and the measurement data recorded by the color sensor and/or the hair condition sensor may be transmitted to the circuit device.

In various exemplary embodiments, a series of measurements may be carried out at changing positions by employing the hair condition determining device, e.g. by the user moving the hair condition determining device from the hairline to the hair tips. In various exemplary embodiments, the circuit device may evaluate the measurement data or series of measurements received from the respective sensors itself or transmit them to an external data processing device, either wirelessly or wired, for evaluation. In various exemplary embodiments, an evaluation of the acquired data may include, for example, a graphical representation of hair condition information on a display device of the hair condition determining device and/or an external data processing device. In various exemplary embodiments, the acquired measurement data may also be stored in a storage device of the hair condition determining device and/or the external data processing device.

In various example embodiments, the user of the hair condition determining device may cause the acquired measurement data to be stored by moving the hair condition determining device according to a predefined movement pattern in order to set the hair condition determining device in a storage mode, for example by employing a "fast movement from left to right and again from right to left" of the hair condition determining device before performing a new series of measurements.

In various exemplary embodiments, the hair condition determining device may be set to a standby mode by employing, for example, a "shake out" after a successful execution of at least one recording of sensor measurement values, in that, for example, the color sensor and the hair condition sensor may no longer be supplied with energy and only the acceleration sensor and the circuit device may be supplied with energy, for example, if the hair condition determining device is located in a charging station.

In various exemplary embodiments, it may be made possible that a series of measurements including shades of hair color and degrees of hair damage, and a position where at least one hair color and at least one degree of hair damage has been recorded from hair of a consumer, may be made available for further data post-processing.

In various exemplary embodiments, the hair condition determining device can make it possible to compare the results of the measurement series when a plurality of measurement series are repeatedly carried out on the hair of a constant consumer after a predefined time, for example, to be able to track or determine progress with regard to minimizing the degree of hair damage to the consumer's hair through the use of suitable hair care products.

In various exemplary embodiments, the device may exchange information with a memory for managing hair condition information via a data link, e.g. measured values concerning hair color and/or degree of hair damage. The memory may be a large data storage, for example a data server, a cloud server, an analysis platform such as the Constant Information Miner Server (KNIME server) or a Big Data KNIME server. By using a KNIME server, systematic applications of statistical methods to large amounts of data may be realized, whereby the large amounts of data, also known as "big data" or mass data, cannot be evaluated with manual or conventional data processing methods. By using a KNIME server, for example, a simple and fast connection of modules for the data preprocessing of user data may be realized using a graphical user interface. By using a KNIME server and big data, for example, new cross links and trends in the care product industry may be determined.

The designs and advantages described here refer to the device and the method. Exemplary embodiments of the present disclosure are shown in the figures and are explained in more detail below. The descriptions of the figures are repeated below for reference.

Figure 2:
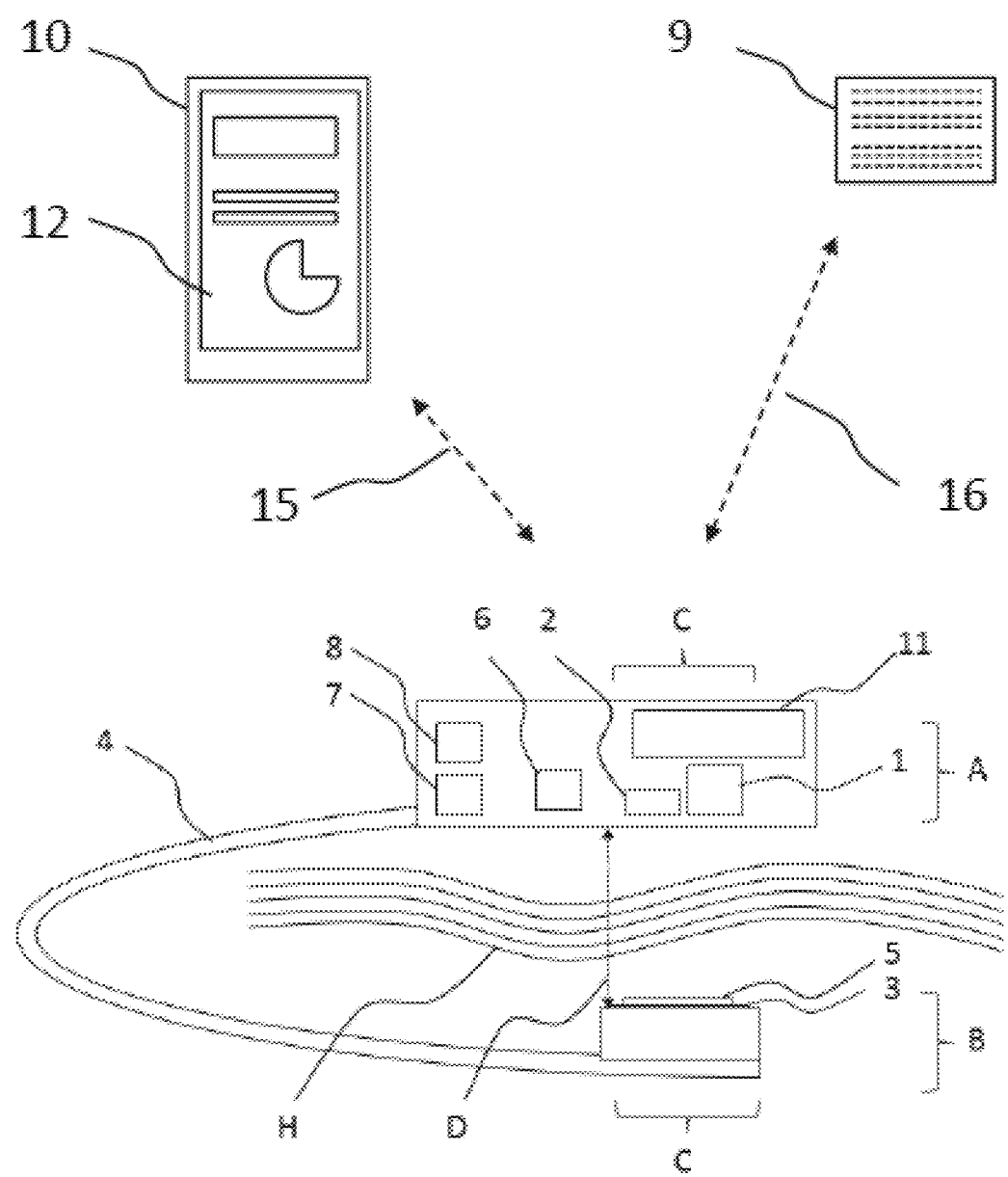
FIG. 2 is a schematic illustration of a hair condition determining device for providing hair condition information according to different exemplary embodiments.
Figure 3A:
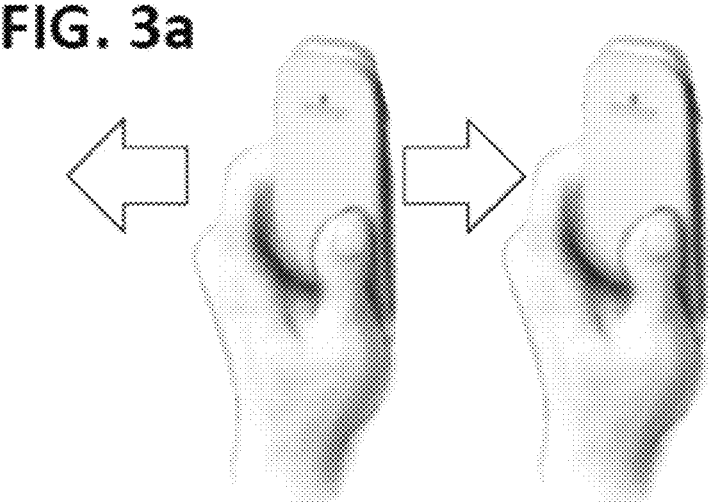
FIGS. 3a, 3b, and 3c are exemplary operations of a hair condition determining device for providing hair condition information according to different exemplary embodiments.
Figure 3B:
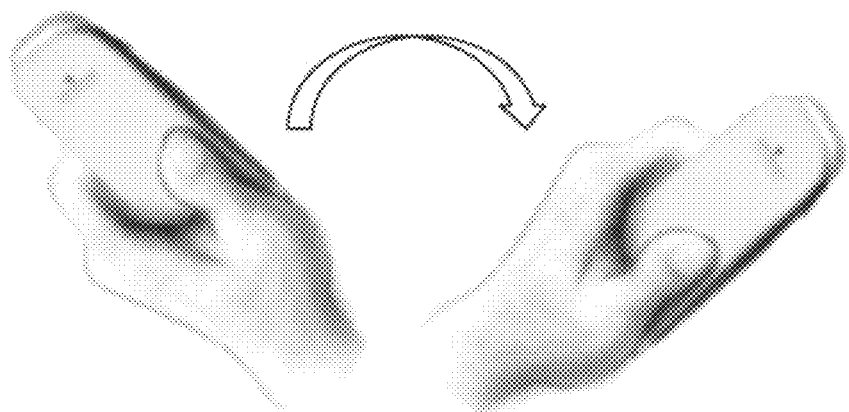
Figure 3C:
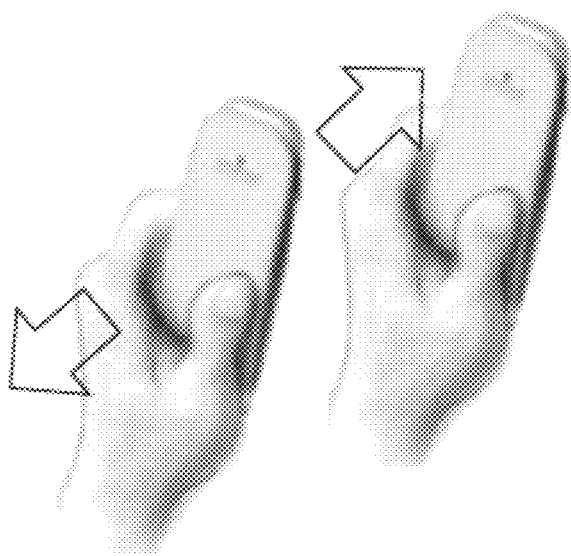
Figure 4:
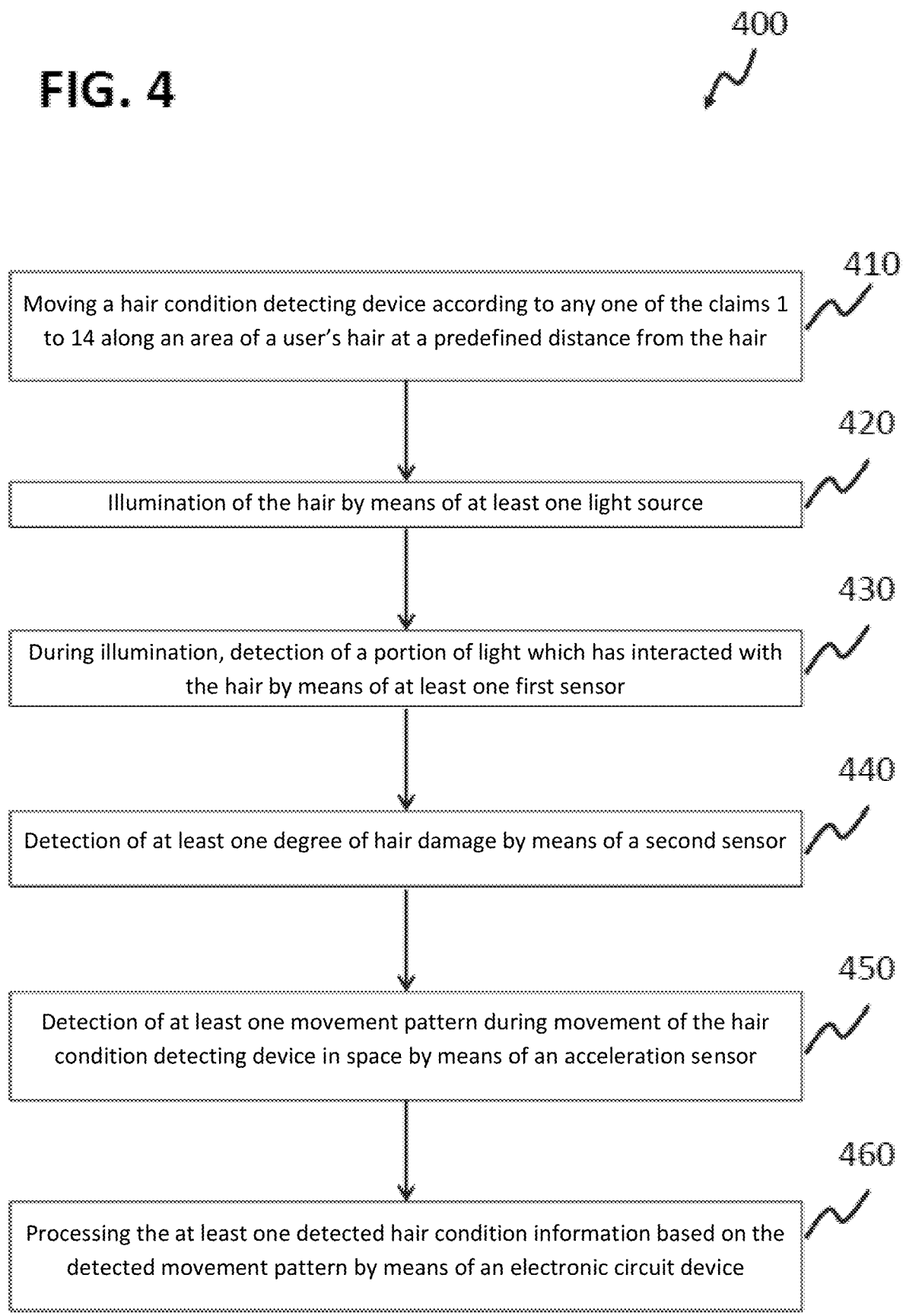
FIG. 4 is an exemplary flow chart of a method for providing hair condition information according to different exemplary embodiments.

FIG. 1 is a schematic side view of a hair condition determining device for providing hair condition information according to different exemplary embodiments;

FIG. 2 is a schematic illustration of a hair condition determining device for providing hair condition information according to different exemplary embodiments;

FIGS. 3a, 3b, 3c are an exemplary operation of a hair condition determining device for providing hair condition information according to different exemplary embodiments; and FIG. 4 is an exemplary flow chart of a method for providing hair condition information according to different exemplary embodiments.

In the following detailed description, reference is made to the attached drawings which form part of the present application and which, for illustration, show specific exemplary embodiments in which the present disclosure may be applied In this respect, directional terminology such as "top", "bottom", "front", "back", "forward", "backward", etc. is used in relation to the orientation of the Figure(s) described. Since components of exemplary embodiments may be positioned in a number of different orientations, the directional terminology is used for illustration purposes and is not restrictive in any way. It goes without saying that other exemplary embodiments may be used and structural or logical changes may be made without deviating from the scope of protection of the present disclosure.

Furthermore, it goes without saying that the features of the various exemplary embodiments described herein may be combined, unless specifically stated otherwise.

The following detailed description is therefore not to be understood in a restrictive sense and the scope of protection of the present disclosure is defined by the attached claims.

A digital image herein may be understood to be a data packet which may be represented by a data processing system as a two-dimensional set-up of pixels, for example in a coordinate system having an x-axis and a y-axis, each pixel being associated with at least one color information which may be represented as the color of a pixel of a monitor or a printed dot of a printed image. The digital image may, for example, be a photograph taken with a digital camera or a single frame of a video sequence taken with a digital camera.

In this context, a "color" may be understood as a combination of a shade of color (i.e. a spectral color impression, also known as hue, which may be understood as what is regarded as the "actual color"), a color intensity (i.e. how intense the color appears, e.g. compared to a neutral gray, which is also known as saturation, color saturation, chromaticity, chromaticity or color depth) and a brightness (i.e. how light or dark the color appears).

In various exemplary embodiments, the color information may be parameterized in a known color space, for example in an L*a*b* color space (where L* indicates the brightness of a color, a* the green and red components and b* the blue and yellow components of the color), in an RGB color space by color components in red, green and blue, in a CMYK color space by color components in cyan, magenta, yellow and black, or in any other color space.

The term "hue" may be understood herein as a color value or the spectral color impression of a color, regardless of how it may be parameterized, for example as a point in a two-dimensional color space (e.g. a*b* of the L*a*b* system) or a ratio of color components (as in the RGB color space or the CMYK color space).

In various exemplary embodiments, a color space from which the color information (hair color information and image color information) originates may be such that a determined or represented color is independent of a medium through which the color is determined or represented (e.g. screen, printer, scanner, human eye, etc.). The color space may be, for example, an L*a*b* color space, the color information a shade of color parameterized by employing a* and b*, for example. The uniform representation in the medium-independent color space makes it possible to present a realistically expected coloring result.

FIG. 1 is a schematic side view of a hair condition determining device to provide hair condition information according to different embodiments.

In various sample embodiments, the hair condition determining device may comprise at least one optical sensor 1, for example a color sensor 1a and a hair condition sensor 1b, in a first area A. In various exemplary embodiments, the first area A may further comprise a light source 2, an acceleration sensor 6, an electronic circuit device 7, a storage device 8 and optionally a display device 11. In various exemplary embodiments the display device 11 may be located on top of the hair condition determining device.

In various exemplary embodiments, the first area A may further comprise a haptic signal generator (vibrator).

In various exemplary embodiments, the first area A may be coupled to a second area B via a connecting element 4. In various exemplary embodiments the connecting element 4 may comprise a U-shaped and elastic spring steel. In various exemplary embodiments, the second area B may comprise a carrier 3 and a calibration medium 5. In various exemplary embodiments, the first area A and the second area B may be positioned at end areas C of connecting element 4. In various exemplary embodiments, a lower surface of the first area A may be at a predefined distance D, for example in a range from about 0 mm to about 200 mm, from the second area B. In various exemplary embodiments, hair H of a consumer may be placed between the first area A and the second area B. In various exemplary embodiments, the light source 2 may be configured to illuminate the opposite carrier 3 and/or the opposite calibration medium 5 during a measurement of hair condition information, for example a hair color and a degree of hair damage. In various exemplary embodiments, a movement or movement pattern 6 may be detected by employing the acceleration sensor 6 and determined by an electronic circuit device 7 by comparing the detected measurement data with at least one known movement pattern. In various exemplary embodiments, at least one recorded sensor measurement data record may be archived or stored by employing the storage device 8. In various exemplary embodiments, at least one hair condition information of a consumer and/or a user of the hair condition determining device may be displayed by employing the display device 11.

In various exemplary embodiments, a hair condition determining device, which is for example in a standby mode (for example, in standby mode only the motion sensor and the circuit device are supplied with power), may be picked up by a user, for example a hairdresser, with one hand, i.e. one hand only. In various exemplary embodiments, the hair condition determining device may detect a change of movement of the hair condition determining device in space by employing at least one acceleration sensor 6 and transmit sensor output measurement data corresponding to a detected movement to an electronic circuit device 7 wirelessly or by wire. In various exemplary embodiments, the circuit device 7 may compare the received measurement data with known motion measurement data and assign them to at least one known motion measurement data record.

In various exemplary embodiments, the circuit device 7 may cause the hair condition determining device in standby mode to activate into an operating mode (for example, in the operating mode, in addition to the motion sensor 6 and the circuit device 7, at least one light source 2 and at least one color sensor 1a and a hair condition sensor 1b are also supplied with energy from a rechargeable battery).

In various exemplary embodiments, the user may move the hair condition determining device according to a predefined movement pattern before performing a series of measurements in order to achieve a shifting of the hair condition determining device into an operational state, e.g. "keeping the hair condition determining device vertical" after removing the hair condition determining device from an external charging station may cause an activation of the hair condition determining device, "holding the hair condition determining device vertical and shaking it" may be used to start a new recording of at least one measurement series, "shaking the hair condition determining device out" may be used to delete a last measurement and/or measurement series from the storage device 7, etc.

In various exemplary embodiments, the hair condition determining device may capture further movement patterns of the user and then process corresponding commands. In various exemplary embodiments, the hair condition determining device may be set up to learn and save newly provided movement patterns, i.e. movements in which the user moves his arm together with the hair condition determining device in a predefined manner or repeatedly moves it in a predefined manner, and to assign them to certain actions that may be performed by the hair condition determining device.

In various exemplary embodiments, the hair condition determining device may be activated by "holding it vertical and shaking" the hair condition determining device before a new measurement series is performed. In various exemplary embodiments, the hair condition determining device may then be parameterized in such a way that it is ready to take at least one new series of measurements and, for example, the color sensor 1a and/or the hair condition sensor 1b and/or at least one light source 2 may be activated on the hair condition determining device. In various exemplary embodiments, the user may attach or apply or move the hair condition determining device to hair H of a consumer in such a way that the hair is located between a first area A, which may, for example, comprise at least one sensor 1 and/or one light source 2, and a second area B, which may comprise at least one carrier 3 and/or one calibration medium 5, and may be held by the first area A and the second area B in a pincer-like manner by employing the manual force of the user without causing damage to the hair.

In various exemplary embodiments, in order to record a plurality of hair condition measurement values by employing the device, the first area A and the second area B may be moved towards each other by the muscle power of the user, while the hair H of a consumer to be measured is located between the first area A and the second area B.

In various exemplary embodiments, the first sensor 1a, for example a color sensor, and/or the second sensor 1b, for example an NIR sensor, may be set to a calibration mode during a calibration process by employing the calibration medium 5 after activation of the color sensor and/or the NIR sensor and a light source 2. In various exemplary embodiments, the calibration medium 5 may then be moved to a predefined distance, for example to a distance of about 0 mm to about 10 mm, towards the opposite color sensor 1a and/or the NIR sensor 1b using muscle power. In various exemplary embodiments, for example, the calibration medium may be positioned directly in front of or directly against a main measuring surface of the NIR sensor during a calibration process of the NIR sensor. In various exemplary embodiments, the color sensor 1a may then use the light source 2 and/or the NIR sensor 1b may use an infrared source (IR source) to illuminate a surface of the calibration medium 5 opposite the sensors 1, for example a ceramic, and detect or measure a reflection (and thus also the absorption) of the reflected light rays and/or infrared rays. In various exemplary embodiments, the color sensor 1a and/or the NIR sensor 1b may then generate an internal calibration profile for all further measurements.

In various exemplary embodiments, the hair condition determining device may be used to carry out a hair condition measurement at one point on the hair and the measurement data recorded by the color sensor 1a and/or the hair condition sensor 1b may be transmitted to the circuit device 7.

In various exemplary embodiments, the first sensor 1a, for example a color sensor, and/or the second sensor 1b, for example an NIR sensor, may emit light when the light source 2 and/or infrared source are switched on, which may fall on a consumer's hair, whereby the emitted light is reflected back by the hair or on the hair. In various exemplary embodiments, the reflected light rays and/or infrared rays may be detected or measured by the sensors 1 and stored in the storage device 8, for example. In various exemplary embodiments, a multi-channel color measurement with transformation into a representation space, for example CIE LAB, may be carried out using color sensor 1a.

In various exemplary embodiments, a series of measurements may be carried out at changing positions by employing the hair condition determining device, e.g. by the user moving the hair condition determining device from the hairline to the hair tips. In various exemplary embodiments, the circuit device 7 may evaluate the measurement data or series of measurements received from the respective sensors 1a, 1b by itself or transmit them wirelessly or by wire to at least one external data processing device 10 for evaluation. In various exemplary embodiments, an evaluation of the acquired data may comprise, for example, a graphical representation of hair condition information on a display device 11 of the hair condition determining device and/or an external data processing device 12. In various exemplary embodiments, the acquired measurement data may also be stored in a storage device 8 of the hair condition determining device and/or the external data processing device 10.

In various exemplary embodiments, the user of the hair condition determining device may cause the acquired measurement data to be stored by moving the hair condition determining device according to a predefined movement pattern in order to put the hair condition determining device into a storage mode, for example by employing a "fast movement from left to right and again from right to left" of the hair condition determining device before performing a new measurement series.

In various exemplary embodiments, the hair condition determining device may be set to a standby mode, for example by employing a "shaking out" after a successful execution of at least one recording of sensor measurement values, in that, for example, the color sensor 1a and the hair condition sensor 1b and the light source 2 and the infrared source may no longer be supplied with energy and only the acceleration sensor 6 and the circuit device 7 may be supplied with energy, for example, if the hair condition determining device is located in a charging station.

FIG. 2 shows a schematic representation of a device for providing hair condition information according to different exemplary embodiments.

In various exemplary embodiments, the hair condition determining device may include a data transmission module by employing which acquired measurement data may be transmitted via a connection 15, e.g. a wireless connection, to at least one external data processing device 10, e.g. a smartphone or tablet. In various exemplary embodiments, the measurement data transmitted to the external data processing device 10 may be graphically represented, for example, by employing a display device 12. In various example embodiments, the hair condition determining device may have a data transmission module, by employing which acquired measurement data may be transmitted to at least one external storage device 9 via a connection 16, for example a wireless connection. In various exemplary embodiments, the data transmission module may be the same and the data transmission via connections 15 and 16 may be realized simultaneously.

FIGS. 3a, 3b, 3c illustrate an exemplary operation of a hair condition determining device for the provision of hair condition information by a user according to different exemplary embodiments.

FIG. 3a shows a movement pattern where the user first holds the hair condition determining device vertically and then shakes it horizontally from left to right. This movement pattern may be recognized or registered by the circuit device 7. The hair condition determining device may then be configured in such a way that it is ready to record a new series of measurements.

FIG. 3b shows a movement pattern where the user "shakes out" the hair condition determining device, for example, about one axis to cause the hair condition determining device to delete previously acquired measurement data or at least one measurement series.

FIG. 3c illustrates another exemplary movement pattern, where the user may, for example, cause the hair condition determining device to transmit measured data to an external data processing device 10.

FIG. 4 shows an exemplary flow chart of a method for providing hair condition information according to different exemplary embodiments.

The method for providing hair condition information may be used in various exemplary embodiments, e.g. movement with a hair condition determining device according to one of Claims 1 to 14 along an area of a user's hair at a predefined distance from the hair, illuminating the hair by employing at least one light source, detecting during the illumination a part of light which has interacted with the hair by employing at least one first sensor, detecting at least one degree of hair damage by employing a second sensor, detecting at least one movement pattern during a movement of the hair condition determining device in space by employing an acceleration sensor, and processing the at least one detected hair condition information based on the detected movement pattern by employing an electronic circuit device.

The features and advantages described herein in relation to the hair condition determining device are of course also related to the method described herein and vice versa.

Various aspects of this disclosure will be illustrated below:

Exemplary embodiment 1 is a hair condition determining device for providing hair condition information. The device may have a first area and a second area configured to allow a user's hair to be moved between the first area and the second area, wherein in the first area at least one optical sensor for detecting light from a light source as the hair condition information is positioned, wherein the second area comprises at least one carrier, and wherein the first area and the second area are coupled by employing a connecting element such that the first area and the second area face each other in such a way that a main sensor measuring direction of the at least one sensor is oriented at a predefined angle to a surface of the carrier, wherein the connecting element is a hair condition determining device for providing hair condition information.

In exemplary embodiment 2, the subject-matter of exemplary embodiment 1 may optionally show that the connecting element comprises an elastic material.

In exemplary embodiment 3, the subject-matter of exemplary embodiments 1 or 2 may optionally show that the connecting element has a U-shaped configuration and the first area and the second area are each positioned at an end area of the U-shaped configuration.

In exemplary embodiment 4, the subject-matter of exemplary embodiments 1 to 3 may optionally show that at least one calibration medium is positioned on an area of the surface of the carrier facing the first area, wherein the calibration medium is configured to calibrate at least the sensor of the device.

In exemplary embodiment 5, the subject-matter of exemplary embodiment 4 may optionally show that the calibration medium comprises or is a ceramic material.

In exemplary embodiment 6, the subject-matter of exemplary embodiments 1 to 5 may optionally show that the first area comprises a color sensor for detecting a hair color of a user and/or hair damage via UV light by employing absorption or reflection and a hair condition sensor for detecting a degree of hair damage of the user, and wherein the color sensor detects a hair color of the user at a first time and the hair condition sensor detects a degree of hair damage of the user at a second time, and wherein the first time and the second time lie in a predefined time range, and wherein the calibration medium is configured to calibrate at least the sensor of the device.

In exemplary embodiment 7, the subject-matter of exemplary embodiments 1 to 6 may optionally show that the first area or the second area further include an acceleration sensor.

In exemplary embodiment 8 the subject-matter of exemplary embodiment 7 may optionally show that the acceleration sensor is designed to detect a movement condition of the device in space.

In exemplary embodiment 9, the subject-matter of exemplary embodiments 1 to 8 may optionally show that the device further comprises an electronic circuit device.

In exemplary embodiment 10, the subject-matter of exemplary embodiment 9 may optionally show that the circuit device is at least set up to control an operating mode of the device based on at least one movement condition of the device detected by employing the acceleration sensor.

In exemplary embodiment 11, the subject-matter of exemplary embodiment 10 may optionally show that the circuit device is further set up, based on the respective detected movement condition, to store at least one item of hair condition information detected by employing the at least one sensor in a storage device of the device or in an external storage device, and/or to delete at least one item of hair condition information from the storage device of the device or from the external storage device, and/or to transmit the hair condition information to an external data processing device, and/or to display information based on the hair condition information on a display device of the device and/or on a display device of the external data processing device.

In exemplary embodiment 12, the subject-matter of exemplary embodiments 1 to 10 may optionally show that the device further comprises a display device for displaying information based on the at least one hair condition information recorded by employing the device.

In exemplary embodiment 13, the subject-matter of exemplary embodiments 6 to 12 may optionally show that the sensors are operated simultaneously.

In exemplary embodiment 14, the subject-matter of exemplary embodiments 1 to 13 may optionally show that the hair condition sensor comprises a near-infrared spectroscopy sensor and/or a UV/fluorescence sensor and/or a sensor by employing which visible light may be detected.

In exemplary embodiment 15, the subject-matter of exemplary embodiments 1 to 14 may optionally show that the hair condition determining device is part of an ecosystem.

In exemplary embodiment 16, the subject-matter of exemplary embodiments 1 to 15 may optionally show that an individual hair treatment product may be produced for a user by employing the data recorded by the hair condition determining device and/or the determined hair condition.

Exemplary embodiment 17 is a method for providing hair condition information. The method may show moving a hair condition determining device according to one of the example embodiments 1 to 16 along an area of a user's hair at a predefined distance from the hair, illuminating the hair by employing at least one light source, during the illumination, detecting a portion of light that has interacted with the hair by employing at least one first sensor, detecting at least one degree of hair damage by employing a second sensor, detecting at least one movement pattern when the hair condition determining device is moved in space by employing an acceleration sensor, and processing the at least one detected hair condition information based on the detected movement pattern by employing an electronic circuit device.

In exemplary embodiment 18, the subject-matter of exemplary embodiment 17 may optionally indicate that processing includes at least one of the following: storing the hair condition information detected by employing at least one sensor in a storage device upon detection of a first movement pattern, deleting at least one hair condition information stored in the storage device and/or in the external storage device upon detection of a second movement pattern, transmitting the hair condition information to an external data processing device and/or to an external storage device upon detection of a third movement pattern, displaying information based on the hair condition information on a display device of the device and/or on a display device of the external data processing device upon detection of a fourth movement pattern.

In exemplary embodiment 19, the subject-matter of the exemplary embodiments 15 or 18 may optionally show that the method further comprises performing the detection of the hair color at a first time and performing the detection of the degree of hair damage at a second time, wherein the first time and the second time are in a predefined time range.

In exemplary embodiment 20, the subject-matter of exemplary embodiments 17 to 19 may optionally show that detecting the movement pattern comprises comparing the detected movement with a predefined movement pattern by employing an electronic circuit device, and assigning the movement to a predefined movement pattern by employing the circuit device.

In exemplary embodiment 21, the subject-matter of exemplary embodiments 17 to 20 may optionally show that the method further comprises calibrating at least one sensor of the plurality of sensors by employing a calibration medium, wherein the hair condition determining device comprises the calibration medium, wherein the at least one sensor of the plurality of sensors is positioned opposite the calibration medium, and wherein a sensor main measurement direction of the at least one sensor of the plurality of sensors is positioned at a predetermined angle to the calibration medium, and wherein the calibration medium comprises a ceramic material.

In exemplary embodiment 22, the subject-matter of the exemplary embodiment 21 may optionally show that the calibration further comprises merging a first area and a second area of the hair condition determining device such that the first area and the second area are opposite to each other at a predefined distance, wherein in the first area the first sensor and the second sensor are positioned and in the second area 8B the calibration medium is positioned, and while merging, performing the calibration of at least one sensor of the plurality of sensors.

In exemplary embodiment 23, the subject-matter of the exemplary embodiments 1 to 16 may optionally show that the at least one sensor comprises a high-end multi-band sensor or a multi-spectral color sensor.

In exemplary embodiment 24, the subject-matter of exemplary embodiments 17 to 22 may optionally show that the movement pattern comprises a shaking movement of the hair condition determining device by the user of the hair condition determining device and/or the movement pattern comprises a swinging movement of the hair condition determining device by a user of the hair condition determining device.

In exemplary embodiment 25, the subject-matter of exemplary embodiments 1 to 16 may optionally show that the elastic connecting material has a matte and/or matte coated finish.

In exemplary embodiment 26, the subject-matter of exemplary embodiments 1 to 16 may optionally show that a material of the carrier is white or in a white shade in order to enable high reflection.

In exemplary embodiment 27, the subject-matter of exemplary embodiments 1 to 16 may optionally show that the device, if no movement is detected by employing the acceleration sensor, is set into a standby or sleep mode by employing the electronic circuit device.

In exemplary embodiment 28, the subject-matter of exemplary embodiments 1 to 16 may optionally show that the device, if movement is detected by employing the acceleration sensor, is set to an operating mode by the electronic circuit device.

In exemplary embodiment 29, the subject-matter of exemplary embodiments 1 to 16 may optionally show that the first and the second area may be brought together by employing muscle power of a user in such a way that the sensors in the first area and the calibration medium in the second area are opposite each other up to a predefined distance.

In exemplary embodiment 30, the subject-matter of exemplary embodiments 1 to 16 may optionally show that the device comprises at least one rechargeable battery or at least one battery for power supply.

In example embodiment 31, the subject-matter of exemplary embodiments 1 to 14 may optionally show that the connecting element comprises spring steel or plastic material.

In exemplary embodiment 32, the subject-matter of exemplary embodiments 1 to 16 may optionally show that the first area and the second area each comprises an enclosure, the enclosure being configured to enclose and/or seal off the electronic components from the outside.

Exemplary embodiment 33 may comprise a system, wherein the system comprises a device according to one of Claims 1 to 16 and further comprises a mobile data processing device, wherein the mobile data processing device is configured to display at least one item of information based on the determined hair condition information and/or the system further comprises an external database, wherein the database is configured to store the hair condition information detected by employing the at least one sensor.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair condition determining device for providing hair condition information, comprising:
    a first area and a second area configured to allow a user's hair to move between the first area and the second area,
    wherein the first area comprises (i) at least one optical sensor for detecting light from a light source and (ii) a hair condition sensor, the at least one optical sensor comprising a color sensor configured to detect a hair color of the user's hair, the hair condition sensor configured to detect a degree of hair damage of the user's hair,
    wherein the second area comprises at least one carrier and a calibration medium disposed on a surface of the at least one carrier and facing the first area, the calibration medium configured to reflect light from the light source to thereby calibrate the at least one optical sensor, and
    wherein the first area and the second area are coupled by a connecting element in such a way that the first area and the second area are opposite each other in such a way that a sensor main measuring direction of the at least one optical sensor is oriented at a predefined angle to a surface of the at least one carrier,
    wherein:
    the hair condition sensor comprises a near-infrared (NIR) spectroscopy sensor configured to determine the degree of hair damage based on a content of cysteic acid.

2. The hair condition determination device according to claim 1, wherein the connecting element comprises an elastic material.

3. The hair condition determination device according to claim 1, wherein the connecting element shows a U-shaped configuration and the first area and the second area are each positioned at an end area of the U-shaped configuration.

4. The hair condition determination device according to claim 1, wherein the calibration medium comprises a ceramic material.

5. The hair condition determination device according to claim 1, wherein the color sensor is further configured to detect hair damage via UV light by absorption or reflection, and
    wherein the color sensor is configured to detect the hair color of the user's hair at a first time and the hair condition sensor is configured to detect the degree of hair damage of the user's hair at a second time, and
    wherein the first time and the second time lie in a predefined time range.

6. The hair condition determination device according to claim 1, wherein the first area or the second area further comprises an acceleration sensor.

7. The hair condition determination device according to claim 6, wherein the acceleration sensor is configured to detect a movement condition of the hair condition determination device in space.

8. The hair condition determination device according to claim 7, wherein the hair condition determination device further comprises an electronic circuit device.

9. The hair condition determination device according to claim 8,
    wherein the electronic circuit device is at least configured to control an operating condition of the hair condition determination device based on at least one movement condition of the hair condition determination device detected by the acceleration sensor.

10. The hair condition determination device according to claim 9, wherein:
    the electronic circuit device is further configured, based on the detected movement condition,
    to store at least one item of hair condition information detected by the at least one optical sensor in a storage device of the hair condition determination device or in an external storage device, and/or
    to delete at least one hair condition information from the storage device of the hair condition determination device or from the external storage device, and/or
    transmit the hair condition information to an external data processing device, and/or
    to display information based on the hair condition information on a display device of the hair condition determination device and/or on a display device of the external data processing device.

11. The device according to claim 1, further comprising a mixing device configured to produce an individual hair treatment product for the user by utilizing data recorded by the hair condition determining device.

12. A method for providing hair condition information, comprising:
    moving a hair condition determining device along an area of a user's hair at a predefined distance from the user's hair, the hair conditioning determining device comprising a first area and a second area configured to allow the user's hair to move between the first area and the second area, the first area comprising at least one first sensor and at least one second sensor, the second area comprising at least one carrier and a calibration medium disposed on a surface of the at least one carrier and facing the first area;
    illuminating the user's hair with at least one light source;
    during illumination, detecting a portion of light which has interacted with the user's hair with the at least one first sensor, the at least one first sensor comprising a color sensor configured to detect a hair color of the user's hair;
    detecting at least one degree of hair damage by utilizing the at least one second sensor, the at least one second sensor comprising a near-infrared (NIR) spectroscopy sensor configured to determine the at least one degree of hair damage based on a content of cysteic acid;
    detecting at least one movement pattern during a movement of the hair condition determining device in space by utilizing an acceleration sensor; and
    processing of a detected hair condition information based on the detected at least one movement pattern by utilizing an electronic circuit device, wherein:
the calibration medium is configured to reflect light from the light source to thereby calibrate the at least one first sensor, and
the first area and the second area are coupled by a connecting element in such a way that the first area and the second area are opposite each other in such a way that a sensor main measuring direction of the at least one first sensor is oriented at a predefined angle to a surface of the at least one carrier.

13. The method according to claim 12, wherein the processing comprises at least one of the following:
storing the detected hair condition information in a storage device upon detection of a first movement pattern;
deleting at least one of the detected hair condition information stored in the storage device upon detection of a second movement pattern;
transmitting the detected hair condition information to an external data processing device and/or to an external storage device when a third movement pattern is detected; and
displaying information based on the detected hair condition information on a display device of the hair condition determining device and/or on a display device of the external data processing device upon detection of a fourth movement pattern.

14. The method according to claim 12, the method further comprising:
performing a detection of a hair color at a first time; and
performing the detection of the at least one degree of hair damage at a second time, the first time and the second time being within a predefined time range.

15. The method according to claim 14, wherein:
performing the detection of the hair color at the first time comprises detecting the portion of light which has interacted with the user's hair with the first sensor.

16. The method according to claim 12, further comprising:
producing an individual hair treatment product for the user by utilizing data recorded by the hair condition determining device.

17. The method according to claim 16, wherein producing the individual hair treatment product comprises producing the individual hair treatment product specifically designed to reduce the hair damage of the user.

18. The method according to claim 12, wherein:
moving the hair condition determining device along the user's hair comprises placing the user's hair between the first area and the second area of the hair condition determining device.

19. The method according to claim 18, wherein:
the first area and the second area are coupled by a connecting element.

* * * * *